United States Patent [19]

Kornblum

[11] 3,962,053

[45] June 8, 1976

[54] NITRO GROUP DISPLACEMENT

[75] Inventor: Nathan Kornblum, West Lafayette, Ind.

[73] Assignee: Purdue Research Foundation, West Lafayette, Ind.

[22] Filed: June 13, 1973

[21] Appl. No.: 369,635

Related U.S. Application Data

[63] Continuation-in-part of Ser. No. 99,696, Dec. 18, 1970, abandoned.

[52] U.S. Cl............................ 204/158 R; 260/464; 260/465 D; 260/465.1; 260/465.4; 260/468 G; 260/468 H; 260/468 J; 260/471 R; 260/478; 260/485 J; 260/491; 260/590 R; 260/592; 260/644; 260/645; 424/304; 424/311; 424/349

[51] Int. Cl.$^2$................ B01J 1/10; C07C 121/16; C07C 120/00; C07C 76/02

[58] Field of Search................ 260/464, 465.1, 478, 260/491, 485 J, 468 S, 468 G, 465.4, 465 D, 468 H, 471, 490, 590, 592, 644, 204, 158 R

[56] References Cited
UNITED STATES PATENTS

| | | | |
|---|---|---|---|
| 2,528,928 | 11/1950 | Weisblat et al.............. | 260/465.4 X |
| 2,918,489 | 12/1959 | Gold et al....................... | 260/465.4 |
| 2,928,866 | 3/1960 | Vanneman et al......... | 260/465.8 R X |
| 2,990,411 | 6/1961 | Feuer et al............... | 260/465.8 R X |

OTHER PUBLICATIONS

Kornblum, et al., J. A. C. S., vol. 92, pp. 2783–2785, Sept. 23, 1970.

*Primary Examiner*—Joseph Paul Brust
*Attorney, Agent, or Firm*—Leroy Whitaker; Everet F. Smith

[57] ABSTRACT

Esters, ketones, nitriles and nitro compounds bearing an $\alpha$-nitro substituent react with certain salts of aliphatic nitro compounds with displacement of the $\alpha$-nitro substituent. The resulting products are esters, ketones, nitriles and nitro compounds bearing a $\beta$-nitro substituent. Very good yields of the products are obtained when the reaction is run in an aprotic solvent. The $\beta$-nitro products are useful in the treatment of various plant pathogens. The method is applicable to the preparation of a variety of $\beta$-nitroesters, $\beta$-nitroketones, $\beta$-nitronitriles and $\alpha,\beta$-dinitro compounds. Many of these $\beta$-nitro compounds are novel compounds not known heretofore.

4 Claims, No Drawings

NITRO GROUP DISPLACEMENT

CROSS-REFERENCE

This application is a continuation-in-part of my copending application Ser. No. 99,696, filed Dec. 18, 1970 now abandoned.

BACKGROUND OF THE INVENTION

This invention pertains to the reaction of nitro compounds. More particularly, this invention pertains to the displacement of the α-nitro group of α-nitroesters, α-nitroketones, α-nitronitriles and α,α-dinitro compounds by treatment with certain salts of aliphatic nitro compounds.

The displacement of the aliphatic nitro group of α,p-dinitrocumene by a number of anions has been reported by Kornblum et al., *J. Am. Chem. Soc.*, 90, 6219 (1968). This displacement reaction is ascribed to the facility with which radial anions are formed in nitro aromatic systems. A similar displacement reaction also has been reported for α,m-dinitrocumene by Kornblum et al., *J. Am. Chem. Soc.*, 90, 6221 (1968). In both instances the presence of the aromatic nitro group is necessary in order to get displacement of the aliphatic nitro group.

Seigle and Hass, *J. Org. Chem.*, 5, 100(1940), reported the reaction of the sodium salt of nitrocyclohexane with 2-bromo-2-nitropropane to give 1-(1-methyl-1-nitroethyl)-1-nitrocyclohexane. From the sodium salt of 2-nitropropane and 2-bromo-2-nitropropane they obtained 2,3-dimethyl-2,3-dinitrobutane. Other compounds prepared in like manner were 2,3-dimethyl-2,3-dinitropentane and 3,4-dimethyl-3,4-dinitrohexane. The method is limited to the preparation of α,β-dinitro compounds, and only low yields were reported.

A series of nitro malonic esters have been prepared by van Tamelan and Van Zyl by reaction of the appropriate sodio malonic ester with 2-chloro-2-nitropropane. The reported compounds have the formula

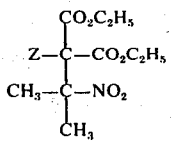

wherein Z is methyl, ethyl, allyl, n-butyl, i-butyl, or i-amyl. This process is also limited in that a malonic ester must be used.

It is also known to prepare symmetrical α,β-dinitro compounds by a dimerization reaction of mononitro compounds.

Tilney-Bassett and Waters, *J. Chem. Soc.*, 1957, 3129, obtained 2,2,3-trimethyl-3-nitrobutyronitrile in poor yield by heating sodio 2-nitropropane with α-nitroisobutyronitrile under reflux in dry alcohol. The exact yield was not reported but the implication was that is was extremely low, and certainly so low that the reaction had no practical significance. The reaction was incidental to the work being reported and no details were given. There was no suggestion that the reaction could be extended to other compounds.

SUMMARY

I have now discovered that when an α-nitroester, α-nitroketone, α-nitronitrile, or α,α-dinitro compound is treated with certain salts of aliphatic nitro compounds in a polar, aprotic solvent the α-nitro substituent is displaced by the aliphatic nitro anion to yield a β-nitroester, β-nitroketone, β-nitronitrile or α,β-dinitro compound. The process is preferably conducted at a temperature of 0° to 50° C. This method makes it possible to obtain novel β-nitroesters, β-nitroketones, and β-nitronitriles which heretofore could not be prepared.

The nitro compounds obtained by this method have been found to exhibit activity against plant pathogens.

DESCRIPTION OF THE PREFERRED EMBODIMENT

The α-nitroester, α-nitroketone, α-nitronitrile or α,α-dinitro compound to be used in my process is one having the formula

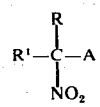

wherein A is $-CO_2Q$, $-CN$, $-NO_2$, or

R separately is $C_1-C_4$ nontertiary alkyl, $C_4-C_6$ cycloalkyl or phenyl;

$R^1$ separately is $C_1-C_4$ nontertiary alkyl, $C_4-C_6$ cycloalkyl, phenyl, $-CO_2Q$ or $-CN$;

or R and $R^1$ taken together with the carbon atom to which they are attached form a $C_4-C_6$ cycloalkyl ring;

Q is $C_1-C_6$ alkyl or phenyl; and $Q^1$ is phenyl or $C_4-C_8$ tertiary alkyl.

When A is an ester group it can be a phenyl or lower alkyl ester such as the methyl, ethyl, isopropyl, secondary butyl or n-hexyl ester. When A is a keto group it should be one having no alpha hydrogen atoms. Thus $Q^1$ in the formula may be such as phenyl, t-butyl, t-amyl or 2-ethyl-2-hexyl.

R when taken separately may be a nontertiary alkyl group of from 1 to 4 carbon atoms, a cycloalkyl group of from 4 to 6 carbon atoms or a phenyl group. Examples of R include methyl, ethyl, isopropyl, sec-butyl, cyclobutyl, cyclohexyl and phenyl.

$R^1$ taken separately may have the same values as R defined above and in addition may be a cyano or ester group. The ester may again be a phenyl or lower alkyl ester.

Preferably, R and $R^1$ separately are lower alkyl, or taken together form a cycloalkyl ring.

Typical α-nitro compounds to be used as starting materials in my process are those set forth in the following tables.

Table 1

| A | R | R' |
|---|---|---|
| $CO_2C_2H_5$ | $CH_3$ | $CH_3$ |
| $COC_6H_5$ | $CH_3$ | $CH_3$ |
| $CN$ | $CH_3$ | $CH_3$ |
| $NO_2$ | $CH_3$ | $CH_3$ |
| $CO_2C_6H_5$ | $CH_3$ | $C_6H_5$ |
| $CO_2C_2H_5$ | $CH_3$ | $CO_2C_2H_5$ |
| $COC_6H_4CH_3$ | $CH_3$ | $CH_3$ |
| $COC_6H_4OCH_3$ | $CH_3$ | $CH_3$ |
| $COC_6H_4Cl$ | $CH_3$ | $CH_3$ |

Table 1-continued

| A | R | R' |
|---|---|---|
| CN | $C_4H_9$ | cyclohexyl |
| CN | $C_6H_5$ | $C_2H_5$ |
| $CO_2C_2H_5$ | cyclopentyl | CN |

Table 2

| A | (R plus R')* |
|---|---|
| $CO_2C_2H_5$ | cyclohexyl |
| $COC_6H_5$ | cyclohexyl |
| CN | cyclopentyl |
| $NO_2$ | cyclohexyl |
| $CO_2C_2H_5$ | cyclobutyl |
| $CO_2C_2H_5$ | cyclopentyl |
| $CO_2CH_3$ | cyclohexyl |
| $COC_6H_5$ | cyclobutyl |
| $COC_6H_5$ | cyclopentyl |

*R and R' taken together with the carbon atom to which they were attached.

The second reactant to be employed in my process is a salt of a nitro compound having the formula

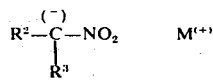

wherein
R² separately is $C_1$-$C_4$ nontertiary alkyl or phenyl;
R³ separately is $C_1$-$C_4$ nontertiary alkyl, phenyl or hydrogen;
or R² and R³ taken together with the carbon to which they are attached form a $C_4$-$C_6$ cycloalkyl ring;
and M is lithium, sodium, or potassium.

Thus, this second reactant is the lithium, sodium, or potassium salt of a nitro compound in which the nitro group is attached to an aliphatic carbon atom. The preferred salt is the lithium salt.

In the formula R² may be phenyl or a lower alkyl group such as methyl, ethyl, propyl, or sec-butyl. R³ may also be phenyl or a lower alkyl group, and in addition may be hydrogen. R² and R³ together with the carbon atom to which they are attached may form a $C_4$-$C_6$ cycloalkyl ring such as cyclobutyl, cyclopentyl or cyclohexyl. Preferably, R² and R³ separately are lower alkyl or together they form a cycloalkyl ring.

Typical salts that may be used in my process are those shown in the following tables.

Table 3

| M | R² | R³ |
|---|---|---|
| Li | $CH_3$ | $CH_3$ |
| Na | $CH_3$ | $CH_3$ |
| Li | $CH_3$ | $C_2H_5$ |
| Li | $CH_3$ | H |
| K | $CH_3$ | $CH_3$ |
| Li | $C_6H_5$ | $CH_3$ |

Table 4

| M | (R² plus R³)* |
|---|---|
| Li | cyclohexyl |
| Na | cyclohexyl |
| K | cyclohexyl |
| Li | cyclobutyl |
| Li | cyclopentyl |

*R² and R³ taken together with the carbon atom to which they are attached.

The α-nitroesters, α-nitronitriles, α-nitroketones and α,α-dinitro compounds employed as starting materials in my process are prepared by procedures which are known in the art. Such procedures are described for example in U.S. Pat. Nos. 2,791,604 and 2,816,909. In addition, the preparation of α,α-dinitro compounds is taught by Kaplan and Shechter, J. Am. Chem. Soc., 83, 3535 (1961). There is a further teaching of the preparation of α-nitroesters by Kornblum et al., Ibid, 79, 2507 (1957). The preparation of α-nitronitriles is taught by Kornblum et al., Ibid, 92, 5783 (1970) and α-nitroketones are taught by Hurd et al., J. Org. Chem., 20, 927 (1955); Simmons et al., Ibid, 31, 2400 (1966); and Simmons et al., Ibid, 33, 836 (1968).

U.S. Pat. No. 3,038,015 (June 5, 1962) teaches the preparation of nitroparaffins. Salts of such nitroparaffins are then prepared as taught hereinbelow.

The preparation of salts of aliphatic nitro compounds is described by Kerber et al., J. Am. Chem. Soc., 87, 4520 (1965). In accordance with the procedure there described a lithium ethoxide solution was prepared by the careful addition of 0.78 g. of lithium hydride to 100 ml. of absolute ethanol. After the solution had become clear 9.00 g. of 2-nitropropane was added and the solution was transferred to a one liter round-bottom flask and stripped at room temperature on a rotary evaporator. When the solution became viscous, but before precipitation of the salt began, about 700 ml. of absolute ether was added to cause precipitation. The resultant slurry was filtered in a nitrogen-filled glove box and the precipitate was washed with ether and transferred to a 200 ml. round-bottom flask. It was subjected to vacuum overnight, crushed and kept under oil-pump vacuum for another 24 hours. Potentiometric titration of weighed samples with ethanolic picric acid showed a neutralization equivalent of 95.5 (theoretical neutralization equivalent 95.0).

In an alternate procedure for salt formation, lithium metal is reacted with methanol, the aliphatic nitro compound is added, the solution is concentrated to a syrup, and the salt is precipitated by dilution with cyclohexane. The salt is then dried in the manner described in the preceding paragraph.

It is a feature of my process that a polar, aprotic solvent is employed. Polar, aprotic solvents as a class are well known to those skilled in organic chemistry. Examples of such solvents include dimethylformamide, dimethylsulfoxide, hexamethylphosphoramide, diethylacetamide, N-methylpyrrolidone, and acetonitrile. The use of such a solvent results in excellent yields which may exceed 90 percent, as opposed to the very poor yield obtained by Tilney-Bassett and Waters by their process which employed alcohol as solvent. The preferred solvents are dimethylsulfoxide, hexamethylphosphoramide, and dimethylformamide.

In accordance with my process the α-nitro compound is treated with the salt at a temperature within the range of 0° to 50° C. and preferably within the range of 20° to 35° C. The reaction proceeds quite well at room temperature so that generally there is no need to provide external heating or cooling.

I have found the reaction to be facilitated by light in the visible spectrum. The reaction will proceed in the dark but is somewhat slower than when the light is present. I also prefer to conduct the reaction in an inert atmosphere such as nitrogen. While the reaction is not highly sensitive to oxygen, it is preferred to exclude oxygen.

A molar ratio of salt to α-nitro compound of 1:1 is adequate. Higher ratios of salt to α-nitro compound result in a faster reaction rate.

My invention will be further illustrated by the following examples.

EXAMPLE 1

The lithium salt of 2-nitropropane (14.3 g.) is placed in a dry flask fitted with a stirrer and a rubber stopple. The system is swept with nitrogen for a half hour and then 375 ml. of dimethylsulfoxide (distilled from calcium hydride and stored under nitrogen) is introduced through the stopple using a hypodermic syringe. This is followed by the addition of 12.43 g. of ethyl α-nitroisobutyrate and the nitrogen flow is terminated. The stirred mixture is exposed to two 20-watt fluorescent lights for eleven hours after which time the resulting yellow solution is poured into ice water and extracted with ethyl ether. The ether solution is washed with water, dried and evaporated. Distillation of the residue gives 14.87 g. (95 percent yield) of pure ethyl β-nitro-α,α,β-trimethylbutyrate: b.p. (1 mm.), 69.5° to 70° C.; $n_D^{20}$ 1.4456.

Analysis: Calculated for $C_9H_{17}NO_4$: C,53.20; H,8.37; N,6.89; Mol Wt. 203 Found: C,53.6; H,8.56; N,7.12; Mol. Wt. 205.

EXAMPLE 2

The lithium salt of 2-nitropropane (9.9 g.) was dissolved in 200 ml. of hexamethylphosphoramide under nitrogen and ethyl 1-nitrocyclobutanecarboxylate was added. The mixture was stirred for three hours under fluorescent lighting. The mixture was then diluted with 400 ml. of water and extracted three times with 200 ml. portions of ether. The combined ether extracts were washed three times with water, dried over magnesium sulfate, and the ethyl 1-(α-nitroisopropyl)cyclobutanecarboxylate (70 percent yield) was recovered by distillation: b.p. (0.1 mm.), 62° C.

Analysis: Calculated for $C_{10}H_{17}NO_4$: C,55.80; H,7.96; N,6.51 Found: C,55.63; H,8.04; N,5.70.

EXAMPLE 3

The lithium salt of 2-nitropropane (0.52 mol.) was dissolved in 700 ml. of hexamethylphosphoramide and, while under nitrogen, 62.1 g. (0.3 mol.) of 3'-methyl-α-nitroisobutyrophenone was added. The reaction mixture was stirred 18 hours under fluorescent lighting. The mixture was then diluted with 1400 ml. of water and the aqueous mixture was extracted three times with 800 ml. portions of ether. The combined ether extracts were washed three times with water, dried over magnesium sulfate and the ether removed. The residue was crystallized from hexane to give a 48 percent yield of 3-nitro-2,2,3,3'-tetramethylbutyrophenone: m.p. 50°–51° C.

Analysis: Calculated for $C_{14}H_{19}NO_3$: C,67.45; H,7.68; N,5.62 Found: C,67.60; H,7.89; N,5.90.

EXAMPLE 4

To 6 l. of dimethylsulfoxide was added 505 g. of potassium t-butoxide followed by the dropwise addition of 534 g. of 2-nitropropane. After stirring for two hours 483 g. of ethyl α-nitroisobutyrate was added and the mixture was stirred under fluorescent lighting for four days. The reaction mixture was diluted with 12 l. of water and extracted three times with 3 l. portions of ether. The ether was washed three times with water, dried over magnesium sulfate, and the ether removed. The oily residue was distilled to give 490.5 g. (81 percent) of the same product as obtained in Example 1.

Following procedures similar to those of Examples 1 to 4, the compounds in the following tables were prepared.

Table 5

| Ex. No. | Name | b.p., °C. | Calculated C | H | N | Found C | H | N |
|---|---|---|---|---|---|---|---|---|
| 5 | Ethyl α,α-dimethyl-1-nitrocyclohexaneacetate | 91 (0.3 mm.) | 59.23 | 8.70 | 5.76 | 59.20 | 8.82 | 5.94 |
| 6 | Ethyl 2,2,3-trimethyl-3-nitrovalerate | 76 (0.2 mm.) | 55.28 | 8.81 | 6.44 | 55.51 | 8.81 | 6.35 |
| 7 | Ethyl 2,2-dimethyl-3-nitrobutyrate | 75.5 (2.0 mm.) | 50.78 | 7.99 | 7.40 | 51.06 | 8.06 | 7.70 |
| 8 | Ethyl 1-(α-nitroisopropyl)cyclopentanecarboxylate | 78.79 (0.1 mm.) | 57.62 | 8.35 | 6.11 | 57.92 | 8.52 | 6.20 |
| 9 | Ethyl 1-(1-nitroethyl)cyclopentanecarboxylate | 79–80 (0.1 mm.) | 55.80 | 7.96 | 6.51 | 56.02 | 8.19 | 6.80 |
| 10 | Ethyl 2,3-dimethyl-3-nitro-2-phenylbutyrate | 100–110 (0.05 mm.) | 63.38 | 7.22 | 5.28 | 63.24 | 7.07 | 5.40 |
| 11 | Diethyl 2-methyl-2-(α-nitroisopropyl) malonate | 76–78 (0.05 mm.) | 50.56 | 7.33 | 5.36 | 50.58 | 7.49 | 5.28 |

Table 6

| Ex. No. | Name | m.p., °C. | Calculated C | H | N | Found C | H | N |
|---|---|---|---|---|---|---|---|---|
| 12 | Ethyl 1-(2-nitroisopropyl)cyclohexanecarboxylate | 52–53 | 59.23 | 8.70 | 5.76 | 59.30 | 8.75 | 5.84 |
| 13 | Ethyl 1-(1-nitrocyclohexyl)cyclohexanecarboxylate | 89–90 | 63.57 | 8.89 | 4.94 | 63.85 | 9.08 | 4.99 |
| 14 | 2,2,3-Trimethyl-3-nitrobutyrophenone | 54–55 | 66.36 | 7.28 | 5.95 | 66.65 | 7.45 | 6.20 |
| 15 | 1-(1-Nitrocyclohexyl)-1-benzoyl cyclohexane | 125.5–126.5 | — | — | — | — | — | — |
| 16 | 2,2,3-Trimethyl-3-nitrobutyronitrile | 195–196 | 53.80 | 7.68 | 17.99 | 53.83 | 7.61 | 17.85 |
| 17 | α,α-Dimethyl-1-nitrocyclohexaneacetonitrile | 108–109 | 61.19 | 8.21 | 14.28 | 61.33 | 8.06 | 14.07 |
| 18 | 1-Cyano-1-(1-nitroisopropyl)cyclo- | 44–45 | 59.32 | 7.70 | 15.38 | 59.26 | 7.83 | 15.55 |

Table 6-continued

| Ex. No. | Name | m.p., °C | Analyses Calculated C | H | N | Found C | H | N |
|---|---|---|---|---|---|---|---|---|
|  | pentane |  |  |  |  |  |  |  |
| 19 | 1-(1-Methyl-1-nitroethyl)-1-nitro-cyclohexane | 149–150.5 | 49.91 | 7.45 | 12.95 | 50.02 | 7.42 | 12.65 |
| 20 | 2,3-Dimethyl-2,3-dinitrobutane | 208–210 | — | — | — | — | — | — |
| 21 | 1-Nitro-1-(1-nitrocyclohexyl)cyclo-hexane | 214–215.5 | — | — | — | — | — | — |
| 22 | Methyl 1-(2-nitroisopropyl)cyclo-pentanecarboxylate | 65–67 | 59.24 | 8.70 | 5.70 | 59.22 | 8.42 | 5.86 |
| 23 | 3-Nitro-2,2,3,4'-tetramethylbutyro-phenone | 58–60 | 67.45 | 7.68 | 5.62 | 67.40 | 7.90 | 5.47 |
| 24 | 4'-Methoxy-2,2,3-trimethyl-3-nitro-butyrophenone | 48–50 | 63.38 | 7.22 | 5.28 | 63.58 | 7.24 | 5.27 |
| 25 | 4'-Chloro-2,2,3-trimethyl-3-nitro-butyrophenone | 63–65 | 57.89 | 5.98 | 5.19 | 57.94 | 6.26 | 5.43 |
| 26 | 1-(α-Nitroisopropyl)-1-benzoylcyclo-butane | 40–42 | 68.00 | 6.93 | 5.66 | 68.26 | 6.72 | 5.52 |

My process allows the preparation of many β-nitroesters, β-nitroketones, and β-nitronitriles not known heretofore. For example, my novel β-nitroesters are those having the formula

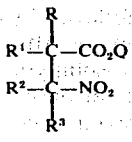

wherein R, R$^1$, R$^2$, R$^3$, and Q are as defined above, except that R$^1$ may not be CO$_2$Q. My novel β-nitroketones have the formula

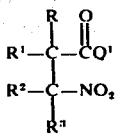

wherein R, R$^1$, R$^2$, R$^3$ and Q$^1$ are as defined above. The novel β-nitronitriles, in turn, have the formula

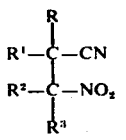

wherein R, R$^1$, R$^2$, and R$^3$ are as defined above, except that all of them may not be methyl at the same time.

The compounds prepared by the process of my invention have been found to be active against foliar diseases of plants. For example, the compounds of Examples 16, 19 and 20 were quite active against bean mosaic virus. The compound of Example 14 was extremely active against crown gall while the compound of Example 17 was extremely active against bacterial blight. The compound of Example 1 exhibited activity against late blight.

In the use of my compounds in the treatment of foliar diseases they are formulated as emulsifiable concentrates, wettable powders, dusts, or granules all in accordance with known procedures. Such formulations include emulsifying agents, solvents, and fillers as is common in the art. The compounds are applied to foliage at rates of from about 0.1 to about 10 pounds per acre. It is preferred to apply my compounds to foliage by spraying, so the preferred formulations are those that result in liquid compositions suitable for spray application.

I claim:
1. A method for the preparation of a compound having the formula

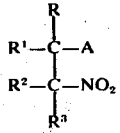

which comprises treating a nitro compound having the formula

with at least one mole of a salt of a nitro compound having the formula

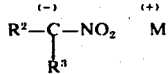

at a temperature within the range of 0° to 50° C. in a polar, aprotic solvent,
wherein A is —CO$_2$Q, —CN, —NO$_2$, or

R separately is C$_1$–C$_4$ nontertiary alkyl, C$_4$–C$_6$ cycloalkyl or phenyl p-chlorophenyl p-methoxyphenyl, p-tolyl;
R$^1$ separately is C$_1$–C$_4$ nontertiary alkyl, C$_4$–C$_6$ cycloalkyl, phenyl, —CO$_2$Q or —CN;
or R and R$^1$ taken together with the carbon to which they are attached form a C$_4$–C$_6$ cycloalkyl ring;
R$^2$ separately is C$_1$–C$_4$ nontertiary alkyl or phenyl;
R$^3$ separately is C$_1$–C$_4$ nontertiary alkyl, phenyl or hydrogen;

or $R^2$ and $R^3$ taken together with the carbon to which they are attached form a $C_4$–$C_6$ cycloalkyl ring;
M is lithium, sodium, or potassium;
Q is $C_1$–$C_6$ alkyl or phenyl; and
$Q^1$ is phenyl or $C_4$–$C_8$ tertiary alkyl.

2. A method as in claim 1 wherein the temperature is within the range of 20° to 35° C.

3. A method as in claim 1 wherein the reaction is conducted in the presence of light in the visible spectrum.

4. A method as in claim 1 wherein the reaction is conducted in an inert atmosphere.

* * * * *

UNITED STATES PATENT AND TRADEMARK OFFICE
CERTIFICATE OF CORRECTION

PATENT NO. : 3,962,053
DATED : June 8, 1976
INVENTOR(S) : Nathan Kornblum

It is certified that error appears in the above-identified patent and that said Letters Patent are hereby corrected as shown below:

Column 1, line 18, "90,6219" should read " $\underline{90}$, 6219".

Column 1, line 38, "Tamelan" should read "Tamelen".

Column 2, line 25, " $-\overset{O}{\underset{\cdot\cdot}{C}}O'$ " should read " $-C\overset{O}{\underset{\cdot\cdot}{Q}}'$ ".

Column 3, line 19, "were" should read "are".

Column 5, line 25, "Mol Wt." should read "Mol. Wt.".

Column 6, line 4, "C,55.63" should read "C,55.65".

Column 5, line 65 "-1-benzoyl" should read "-1-benzoyl-".

Column 8, lines 60 & 61, "$C_4$-$C_6$ cycloalkyl or phenyl p-chlorophenyl p-methoxyphenyl, p-tolyl;" should read "$C_4$-$C_6$ cycloalkyl or phenyl;".

Column 9, line 5, "$Q^1$ is phenyl or $C_4$-$C_8$ tertiary alkyl." should read "$Q^1$ is phenyl p-chlorophenyl, p-methoxyphenyl, p-tolyl, or $C_4$-$C_8$ tertiary alkyl.".

Signed and Sealed this

Fourteenth Day of December 1976

[SEAL]

Attest:

RUTH C. MASON
*Attesting Officer*

C. MARSHALL DANN
*Commissioner of Patents and Trademarks*